United States Patent

Heneghan

[19]

[11] Patent Number: 5,855,214
[45] Date of Patent: Jan. 5, 1999

[54] COSMETIC APPLICATOR USING THERMOPLASTIC ATTACHMENT AND METHOD OF MANUFACTURE

[75] Inventor: James J. Heneghan, North Granby, Conn.

[73] Assignee: Latex Foam Products, Inc., Ansonia, Conn.

[21] Appl. No.: 76,529

[22] Filed: May 12, 1998

[51] Int. Cl.⁶ .................................................. A45D 40/26
[52] U.S. Cl. ........................... 132/320; 132/317; 132/318; 401/25; 15/244.1; 15/145; 604/1
[58] Field of Search .................................... 132/320, 317, 132/318; 300/21; 401/130, 119, 196, 6, 25, 207; 128/156; 15/244.1, 209.1, 145, 244.3; 604/1, 2, 3, 305, 306, 294

[56] References Cited

U.S. PATENT DOCUMENTS

| | | | |
|---|---|---|---|
| 29,099 | 7/1860 | Power | 15/145 |
| 188,227 | 3/1877 | Bacon . | |
| D. 206,641 | 1/1967 | Hill | D83/12 |
| D. 251,013 | 2/1979 | Kettel | D24/2 |
| D. 260,881 | 9/1981 | Kaufman | D24/4 |
| D. 270,762 | 9/1983 | Kaufman | D24/63 |
| D. 273,238 | 3/1984 | Taylor et al. | D28/7 |
| D. 336,955 | 6/1993 | Hadaway | D24/100 |
| 467,599 | 1/1892 | Abundi et al. . | |
| 532,359 | 1/1895 | Bradley . | |
| 982,232 | 1/1911 | Bartholomew . | |
| 1,345,280 | 6/1920 | Sweet . | |
| 1,857,145 | 5/1932 | Funk . | |
| 2,218,738 | 10/1940 | Boysen | 132/84 |
| 2,346,782 | 4/1944 | Piluso | 300/21 |
| 2,491,274 | 12/1949 | McNeill | 128/259 |
| 2,510,490 | 6/1950 | Ager | 128/269 |
| 2,810,150 | 10/1957 | Ellman | 15/244 |
| 2,903,914 | 9/1959 | Tarzian | 74/820 |
| 2,932,277 | 4/1960 | Borah | 118/270 |
| 3,126,006 | 3/1964 | Dowell | 128/356 |
| 3,597,826 | 8/1971 | Shields | 29/208 B |
| 3,605,240 | 9/1971 | Avery, Jr. | 29/208 B |
| 3,798,736 | 3/1974 | Gibbons et al. | 29/208 F |
| 3,951,460 | 4/1976 | Blankschein | 300/21 |
| 4,163,142 | 7/1979 | Descovich et al. | 219/79 |
| 4,401,130 | 8/1983 | Halford et al. | 132/88.5 |
| 4,543,702 | 10/1985 | Wada | 29/434 |
| 4,746,238 | 5/1988 | Levine | 401/196 |
| 4,767,398 | 8/1988 | Blasius, Jr. | 604/1 |
| 4,838,851 | 6/1989 | Shabo | 604/1 |
| 4,856,136 | 8/1989 | Janssen | 15/244.3 |
| 4,887,994 | 12/1989 | Bedford | 604/1 |
| 4,913,682 | 4/1990 | Shabo | 604/1 |
| 4,934,011 | 6/1990 | Haug | 15/145 |
| 4,935,001 | 6/1990 | George | 604/1 |
| 5,003,660 | 4/1991 | Oohinata et al. | 15/244.1 |
| 5,085,633 | 2/1992 | Hanifi et al. | 604/35 |
| 5,123,431 | 6/1992 | Wilson | 132/320 |
| 5,158,532 | 10/1992 | Peng et al. | 604/1 |
| 5,212,847 | 5/1993 | Melcher et al. | 15/244.1 |
| 5,358,480 | 10/1994 | Melcher et al. | 604/1 |
| 5,542,144 | 8/1996 | Forsline | 15/245.1 |

FOREIGN PATENT DOCUMENTS 130170  3/1901  Germany .

*Primary Examiner*—Gene Mancene
*Assistant Examiner*—Philogene Pedro
*Attorney, Agent, or Firm*—St. Onge Steward Johnston & Reens LLC

[57] ABSTRACT

A cosmetic applicator using a thermoplastic attachment and method of manufacture is provided. The cosmetic applicator comprises an elongate wand having a first end, the wand comprising a polymeric material, a tip having an interior cavity with an open-end mouth, the first end of the wand positioned in the interior cavity of the tip, the tip comprising resilient polymeric foam having a plurality of cells and sized to substantially cover the end of the wand, and a thermoplastic material adhered to the first end of the wand and melted into the cells of the foam in the interior cavity of the tip for securing the tip to the first end of the wand.

20 Claims, 2 Drawing Sheets

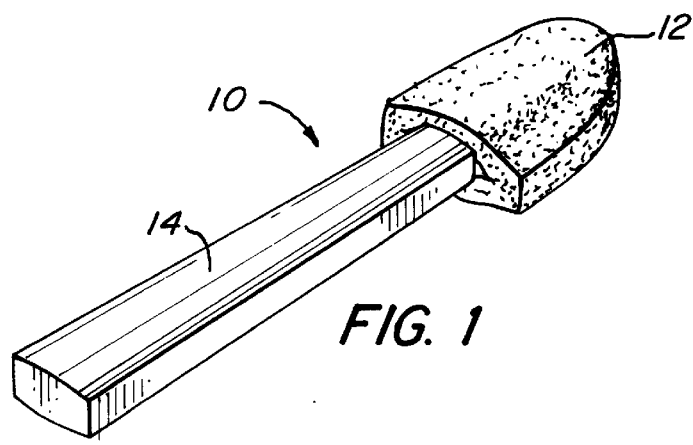
FIG. 1
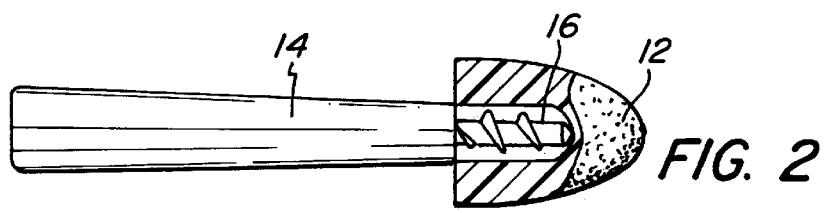
FIG. 2
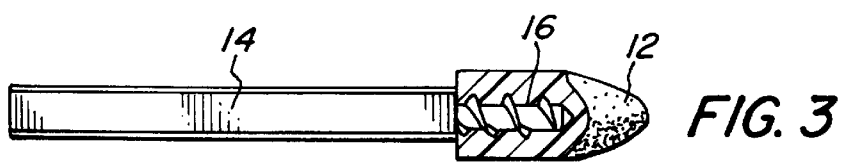
FIG. 3
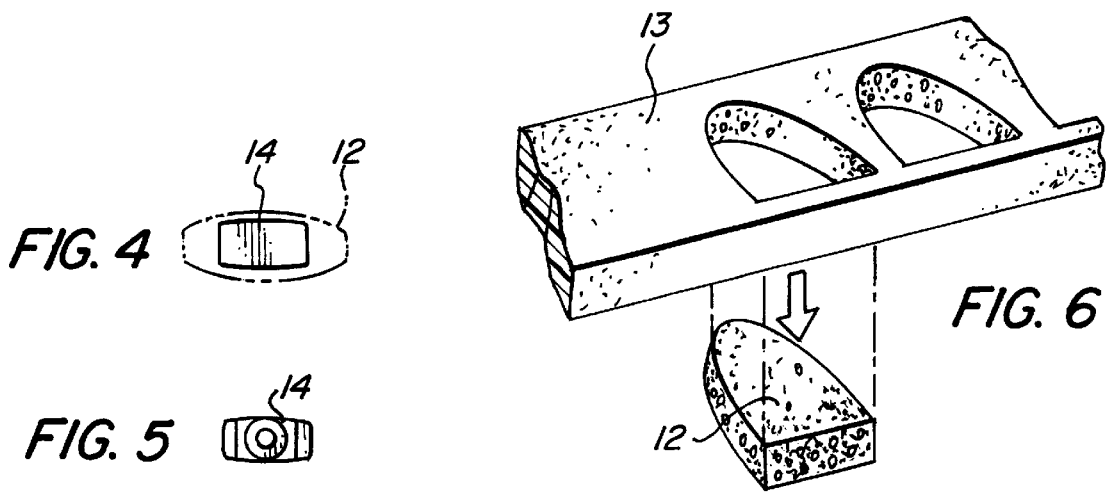
FIG. 4
FIG. 5
FIG. 6

COSMETIC APPLICATOR USING THERMOPLASTIC ATTACHMENT AND METHOD OF MANUFACTURE

FIELD OF THE INVENTION

The present invention relates to applicators that may be used to apply cosmetics, medicine or the like.

BACKGROUND OF THE INVENTION

Conventional applicators have undesirable characteristics in that the handle tends to disconnect from the applicator tip due to deterioration of the adhesive after use or when it is used in a rough manner. There are generally two types of connecting means that give rise to this problem.

In one type of connecting means, adhesive is applied to one end of the handle and then the handle is inserted into an opening in an applicator tip. U.S. Pat. No. 5,003,660 to Oohinata et al. discloses a cosmetic applicator that uses a rubber film adhesive such as synthetic resin. The use of this adhesive is disadvantageous because often times the skin near the eyes is sensitive to adhesives.

U.S. Pat. No. 4,887,994 to Bedford discloses an applicator swab that uses a STABON™ glue or hot melt glue adhesive. The applicator tip, however, has a completed hole through the center of it through which the stick handle is inserted. This hole appears to remain when the applicator is assembled creating an unfinished look. Furthermore, the stick handle may disadvantageously stick out and injure a user of the applicator.

In another type of connecting means, the applicator may be made by preforming an applicator tip then plunging the handle into it. U.S. Pat. No. 5,358,480 to Melcher et al. discloses a swab that uses barbs to secure the applicator tip. This U.S. Pat. No. 4,856,136 to Janssen discloses a foam brush which has extending serrations on the wand to secure the applicator tip. The type of connecting means used in both applicators are insufficient because the use of barbs and serrations alone as an attachment means can lead to the premature disconnection of the applicator tip from the wand if the user should use the tip in a rough manner.

What is desired, therefore, is a cosmetic applicator having a tip that is reliably secured to a wand which does not disconnect even after extended and rough use, wherein the tip is securely attached without the use of an adhesive which can be sensitive to the skin near the eyes, and wherein the tip has a smooth and seamless outer surface.

SUMMARY OF THE INVENTION

Accordingly, it is an object of the present invention to provide a cosmetic applicator having an applicator tip and a wand, wherein the tip is reliably secured to the wand and does not disconnect even after prolonged or rough usage.

It is another object of the present invention to provide a cosmetic applicator that attaches to the applicator tip without the use of an adhesive.

It is still another object of the present invention to provide a cosmetic applicator having a tip with a smooth and seamless outer surface that is not irritating to the user.

It is still a further object of the present invention to provide a cosmetic applicator which is inexpensive to manufacture and which can be quickly and easily assembled.

It is still yet another object of the invention to provide a cosmetic applicator that is composed entirely of hypoallergenic materials.

These objects of the invention are achieved by a cosmetic applicator using a thermoplastic attachment and method of manufacture. The cosmetic applicator comprises an elongate wand having a first end, the wand comprising a polymeric material, a tip having an interior cavity with an open-end mouth, the first end of the wand positioned in the interior cavity of the tip, the tip comprising resilient polymeric foam having a plurality of cells and sized to substantially cover the end of the wand, and a thermoplastic material adhered to the first end of the wand and melted into the cells of the foam in the interior cavity of the tip for securing the tip to the first end of the wand.

BRIEF DESCRIPTION OF THE DRAWINGS

FIG. 1 is an isometric view of an applicator constructed in accordance with the present invention;

FIG. 2 is a top view in partial cross section of the first embodiment of the applicator shown in FIG. 1;

FIG. 3 is a side view in partial cross section of the applicator shown in FIG. 2;

FIG. 4 is a bottom view of a wand of the applicator shown in FIG. 2;

FIG. 5 is top view of a wand of the applicator shown in FIG. 2;

FIGS. 6–10 are schematic views showing the method of assembling the second embodiment of the applicator shown in FIG. 1;

DETAILED DESCRIPTION OF THE INVENTION

A cosmetic applicator (10) using a thermoplastic attachment in accordance with the invention is shown in FIG. 1. The cosmetic applicator (10) comprises an elongated wand (14), an applicator tip (12) and a thermoplastic material (16) attaching the wand to the applicator tip. Frequently, the adhesives used to assemble cosmetic applicators can irritate the skin around the user's eyes. To alleviate this problem, the present invention uses a hypoallergenic thermoplastic material (16) attachment that does not irritate the skin of the typical person.

Figure 10:
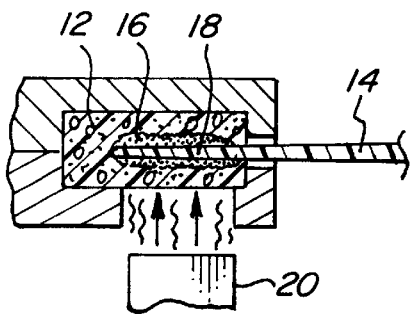
Figure 12:
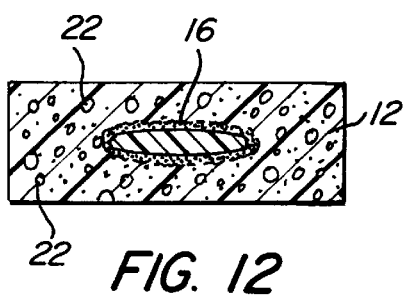
FIG. 12 is a cross sectional view of the applicator shown in FIG. 11 taken along the line A—A.
Figure 11:
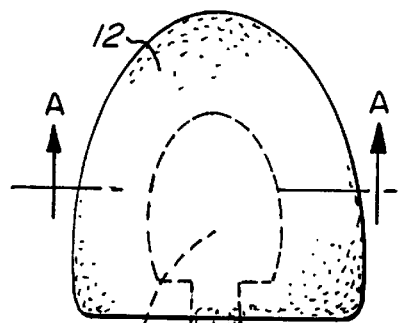
FIG. 11 is a top view of the second embodiment of the applicator.

To provide the thermoplastic attachment, the thermoplastic material (16) is melted and cooled in the area of where the wand is inverted into the tip (FIG. 10). The melted thermoplastic material (16) flows into the open cells (22) of the applicator tip (12) by way of capillary migration and provides an effective attachment when it is cooled (FIGS. 11, 12).

Figure 7:
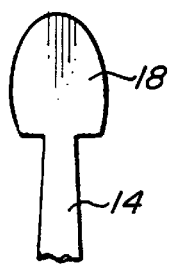

To provide a more effective means for attachment, the head (18) of the wand can have a shape for retaining the applicator tip. For instance, the head (18) can have a paddle head (FIG. 7), a screw head (FIGS. 2, 3) or the head can include barbs to retain the applicator tip (12). The foam of the applicator tip (12) can be shaped to have a buffed profile to provide the user with a gentler applicator surface (FIGS. 2, 3).

Figure 8:
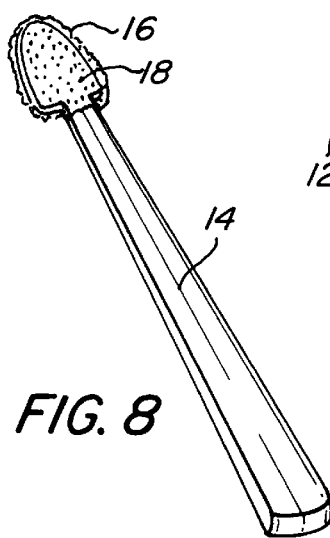
Figure 9:
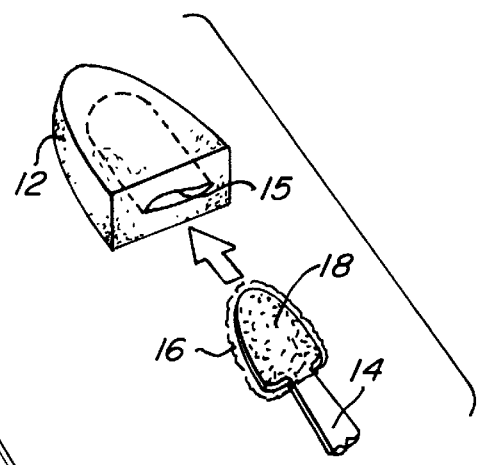

Referring to FIGS. 6–10, the cosmetic applicator is assembled by first punching out a plurality of applicator tips (12) from a sheet of polymeric foam (13), preferably latex foam. Next, a plurality of wands (14) are formed, preferably from a resilient polymeric material. Thermoplastic material (16) is then added to the head (18) of the wand (14) that will accept the applicator tip (12) as shown in FIG. 8. An opening (15) or a slit must be formed in one end of each of the applicator tips (12). The head (18) having the thermoplastic material (16) is then inserted into the applicator tip opening (15) (FIG. 4). As shown in FIG. 10, the applicator tip (12), the wand (14) and the thermoplastic material (16) inside the tip (12) are then heated preferably with forced hot air to a temperature that is above the melting point of the thermoplastic material (16) and less than 180 degrees Fahrenheit, the melting temperature of the applicator tip (12). The thermoplastic material (16) is then allowed to cool.

When the thermoplastic material (16) is melted during assembly, it flows into the open cells (22) of the foam material of the tip (12). When the thermoplastic (16) cools to a solid material, the thermoplastic is embedded in the foam cells (22) of the applicator tip providing an effective attachment between the applicator tip (12) and the wand (14) as shown in FIGS. 11 and 12. The thermoplastic material cools and solidifies quicker than most adhesives.

The thermoplastic material (16) used to attach the applicator tip (12) and the wand (14) must have a melting temperature between the temperature of hot water ordinarily found in a residential home, about 140 degrees Fahrenheit, and the melting temperature of the wand (14), approximately 180 degrees Fahrenheit. The melting temperature of a latex applicator tip (12) is greater than about 250 degrees Fahrenheit. The thermoplastic material (16) can be a material such as polypropylene, acrylic, styrene, cellulosic, vinyl, nylon or a fluorocarbon so long as its melting temperature is approximately between 140 and 180 degrees Fahrenheit, the melted material can migrate through an applicator tip to create an attachment, and the material is hypoallergenic. The preferred type of thermoplastic (16) is Dexter EVA Polyshot Coolmelt, which is a hot melt glue.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. A cosmetic applicator, comprising:
   an elongate wand having a first end, said wand comprising a polymeric material;
   a tip having an interior cavity with an open-end mouth, the first end of the wand positioned in the interior cavity of the tip, the tip comprising resilient polymeric foam having a plurality of cells and sized to substantially cover the end of the wand; and
   a thermoplastic material adhered to the first end of said wand and melted into the cells of the foam in the interior cavity of the tip for securing said tip to the first end of said wand.

2. The applicator according to claim 1 wherein said thermoplastic material has a melting temperature higher than about 140 degrees Fahrenheit and lower than about 180 degrees Fahrenheit.

3. The applicator according to claim 1, wherein the first end of the wand has a head having a shape for mechanically retaining the foam tip on the wand.

4. The applicator according to claim 2, wherein the head shape includes barbs for mechanically retaining the foam tip on the wand.

5. The applicator according to claim 2, wherein the plurality of cells are open cells and said thermoplastic material seeps into some of the plurality of open cells when the thermoplastic material is above its melting temperature.

6. The applicator according to claim 1, wherein the tip comprises latex foam.

7. A cosmetic applicator comprising:
   an applicator tip comprising resilient polymeric foam having a plurality of cells and having a melting temperature higher than about 250 degrees Fahrenheit, the applicator tip having an cavity;
   an elongated wand having a melting temperature of about 180 degrees Fahrenheit having a first end, the first end of the wand positioned inside the cavity of the applicator pad; and
   a thermoplastic material adhered to said first end of the wand and melted into the cells of foam inside the cavity of the applicator pad for attaching the applicator pad to the first end of the wand, said thermoplastic material having a melting temperature higher than about 140 degrees Fahrenheit and lower than about 180 degrees Fahrenheit.

8. The cosmetic applicator according to claim 7, wherein the first end of the wand has a head having a shape for mechanically retaining the foam tip on the wand.

9. The cosmetic applicator according to claim 8, wherein the head shape includes barbs for mechanically retaining the foam tip on the wand.

10. The cosmetic applicator according to claim 7, wherein the tip is capable of absorbing the thermoplastic material at a temperature above its melting temperature.

11. The cosmetic applicator according to claim 7, wherein the applicator pad comprises latex foam.

12. The cosmetic applicator according to claim 7, wherein the wand comprises plastic.

13. A method for making a cosmetic applicator comprising the steps of:
   forming a plurality of applicator tips from polymeric foam having a plurality of cells;
   forming a plurality of elongated wands each having a first end;
   forming a cavity in each of the applicator tips;
   applying a thermoplastic material onto one of the first ends of the wands;
   inserting the first end of the wand having applied thermoplastic into one of the cavities of the applicator tips; and
   heating the thermoplastic, the applicator tip and the first end to a temperature above a melting point of the thermoplastic to flow the thermoplastic into the foam cells and retain the tip on the handle.

14. The method according to claim 13, wherein forming a plurality of applicator tips is done from a single piece of latex foam rubber.

15. The method according to claim 14 further comprising inserting thermoplastic into the cavity and squeezing each of the applicator tips after the thermoplastic has been inserted into each of the cavities so that the thermoplastic is substantially evenly distributed within the applicator tip cavity.

16. The method according to claim 13, further comprising the step of conforming the cavity of each of the applicator tips to the shape of the first end of the wands.

17. The method according to claim 13, further comprising the step of buffing the first end of each of the wands to make a substantially dull end.

18. The method according to claim 13, further comprising the step of retaining either the tip or the wand in tooling after forming a plurality of elongated wands and before forming a cavity in each of the applicator tips.

19. The method according to claim 13, further comprising the step of applying forced air to the intersection area of the applicator tip and the first end to shorten the time for the thermoplastic to cure.

20. The method according to claim 19, wherein heated forced air is applied to shorten the time for the thermoplastic to cure.

* * * * *